US010328027B2

(12) United States Patent
Costa et al.

(10) Patent No.: US 10,328,027 B2
(45) Date of Patent: Jun. 25, 2019

(54) ASSISTED PARTICLE SIZE REDUCTION PROCESS

(71) Applicant: HOVIONE INTERNATIONAL LTD, Wanchai, Hong Kong (CN)

(72) Inventors: Eunice Costa, Santa Iris da Azoia (PT); Marcio Temtem, Quinta do Conde (PT); Luis Sobral, Loures (PT); Constanca Cacela, Lisbon (PT); Peter Villax, Lisbon (PT)

(73) Assignee: Hovione International Ltd., Wanchai (HK)

( * ) Notice: Subject to any disclaimer, the term of this patent is extended or adjusted under 35 U.S.C. 154(b) by 0 days.

(21) Appl. No.: 15/115,193

(22) PCT Filed: Jan. 27, 2015

(86) PCT No.: PCT/GB2015/050186
§ 371 (c)(1),
(2) Date: Jul. 28, 2016

(87) PCT Pub. No.: WO2015/114320
PCT Pub. Date: Aug. 6, 2015

(65) Prior Publication Data
US 2016/0346206 A1    Dec. 1, 2016

(30) Foreign Application Priority Data
Jan. 28, 2014    (PT) ......................................... 107433

(51) Int. Cl.
| | | |
|---|---|---|
| *C07D 225/04* | (2006.01) | |
| *C07D 333/16* | (2006.01) | |
| *C07D 409/12* | (2006.01) | |
| *C07D 413/12* | (2006.01) | |
| *A61K 9/14* | (2006.01) | |
| *A61K 9/00* | (2006.01) | |
| *A61K 31/439* | (2006.01) | |
| *A61K 31/56* | (2006.01) | |
| *A61K 31/522* | (2006.01) | |

(52) U.S. Cl.
CPC .............. *A61K 9/14* (2013.01); *A61K 9/0075* (2013.01); *A61K 9/145* (2013.01); *A61K 31/439* (2013.01); *A61K 31/522* (2013.01); *A61K 31/56* (2013.01)

(58) Field of Classification Search
CPC .. C07D 225/04; C07D 333/16; C07D 409/12; C07D 413/12
USPC ....................................... 549/60, 59, 78, 354
See application file for complete search history.

(56) References Cited

U.S. PATENT DOCUMENTS

2009/0087492 A1    4/2009    Johnson et al.
2010/0266696 A1   10/2010    Muhrer et al.

FOREIGN PATENT DOCUMENTS

| EP | 2050437 A1 | 4/2009 | | |
|---|---|---|---|---|
| JP | A2004-500984 | 1/2002 | | |
| JP | A2011-506400 | 6/2009 | | |
| WO | WO 2011131947 A2 * | 10/2011 | ........... | A61K 9/0075 |
| WO | WO 2013144554 A1 * | 10/2013 | ............... | A61K 9/10 |

OTHER PUBLICATIONS

International Search Report and Written Opinion for International Application No. PCT/GB2015/050186 dated Apr. 5, 2015. (16 pages).
International Preliminary Report on Patentability for International Application No. PCT/GB2015/050186 dated Jun. 5, 2016. (34 pages).
The Pharmaceutics and Compounding Laboratory, Pharmlabs.unc. edu 2018, accessed Feb. 21, 2018. <https://pharmlabs.unc.edu/labs/solubility/intro.htm>.
Solubility Information, Sigma-Aldrich 2018, accessed Feb. 21, 2018. <https://www.sigmaaldrich.com/united-kingdom/technical-services/solubility.html>.
Woods, Appendix Four—BP Solubilities, Pharminfotech.co.nz 2018, accessed Feb. 21, 2018. <http://www.pharminfotech.co.nz/manual/Formulation/mixtures/pages/solubilities.html>.
Office Action, issued by the Japan Patent Office, dated Jul. 24, 2018, Application No. 2016-549143, and English Translation, 11 pgs.

\* cited by examiner

*Primary Examiner* — Matthew P Coughlin
*Assistant Examiner* — Sagar Patel
(74) *Attorney, Agent, or Firm* — Haynes and Boone, LLP

(57) ABSTRACT

A new scalable process to control the particle size and the particle size distribution, comprising 5 steps: (i) suspension preparation in a mixture of solvents in which the API and/or excipient is partially soluble in one of the solvents; (ii) particle size reduction of the suspension; (iii) aging; (iv) stopping the aging by solvent removal; and (v) optionally, a step of isolating the processed ingredients in the form of powder.

25 Claims, 6 Drawing Sheets

ASSISTED PARTICLE SIZE REDUCTION PROCESS

The present application is a national stage entry under 35 U.S.C. § 371 of international PCT application, PCT/GB2015/050186, filed on Jan. 27, 2015, which claims priority to Portuguese Patent Application No. 107433, filed on Jan. 28, 2014.

The present invention describes a process to control the particle size of a chemical product and particularly of a product of pharmaceutical interest, with a high degree of precision. The invention addresses unwanted consequences of the size reduction process, particularly changes in the degree of crystallinity of the polymorphic form of interest.

Controlling particle size with a very high degree of precision has become an important requirement in the pharmaceutical industry, namely in dosage forms used in respiratory inhalation applications but also in other dosage forms where maximizing bioavailability can be achieved through appropriately sized drug particles. In inhalation delivery, there are particle size requirements for respiratory drugs where the precision needed for the median particle size is in the order of ±0.1 micron. This means, for example, that a development specification for particle size might be set at 2.3 micron, with a tolerance of 0.1 micron. Such precise particles specifications allow the targeting of a specific region of the lung and the deposition of drug particles in a well-defined region of therapeutical interest in the bronchi or in the alveoli. Achieving such exquisitely sized particles and controlling the size distribution thereof is an important goal for the pharmaceutical industry.

Therefore, multiple technologies have been developed recently to control the particle size as well as the polymorphic form of interest, and these approaches may be characterized either as bottom up or as top down. Typically, the bottom up approach involves precipitation, crystallization or chemical synthesis while the top down approach uses a particle size reduction technology (e.g. jet milling, wet ball milling, wet polishing) to control both the particle size and the polymorphic form.

In the top down approaches, size reduction usually involves the use of high energy particle-to-particle and/or particle-to-equipment collision, which may impact surface energy and the lattice of the crystalline form. Therefore the output material often contains significant amounts of amorphous or other polymorphic forms influencing both the stability and the performance of the finished products. Several approaches have been described in the literature to address these form changes, particularly in the areas of products of pharmaceutical interest, such as active pharmaceutical ingredients, intermediate drug products and excipients.

A process to reduce the particle size of an active pharmaceutical ingredient (API) while maintaining its polymorphic form, comprising a step of processing the API by cavitation at elevated pressure is described in patent application WO2011131947. In this example, the API is processed in 3 steps: the API is suspended in an anti-solvent where it is insoluble; then it is size-reduced; and it is then preferably dried by spray drying to obtain the product as a dry powder, a technique known as wet polishing (Hovione, Portugal). This patent application only claims the particle engineering of APIs, and excludes the production of intermediate drug products with different polymorphic forms. By particle engineering it is understood a particle size reduction process aiming to attain the target particle size range suitable to the performance of drug products. In this process, polymorphic form and degree of crystallinity control were only achievable under very specific conditions, which not all products are able to meet. Indeed, at the very high pressure required by wet polishing, inevitably a part of the product that was being processed might solubilize, as not all products have a matching perfect anti-solvent. Even when the most appropriate suspension medium is used, residual dissolution could still occur, leading to the decrease of the degree of crystallinity. Anti-solvent selection was also limited by the suitability between API/solvent system and equipment used, leading to processing challenges (e.g. clogging, aggregation) and sometimes even to the over reduction of the particle size. By over reduction it is understood that the particle size of the API is reduced to levels below the target particle size distribution. This leads to batch rejection, a major issue in the pharmaceutical industry. Finally, during the drying phase, the solubilized portion of the product would then become amorphous, leading to changes in product performance, stability profile and a failure in meeting its quality specification.

The present invention describes a new scalable process to control the particle size and the particle size distribution, comprising 5 steps: (i) suspension preparation in a mixture of solvents in which the product of interest is partially soluble in one first solvent and as substantially insoluble in a second solvent; (ii) particle size reduction of the product in suspension leading to a size reduction generally below the desired size; (iii) a step of aging in which crystallization of the partially dissolved product through temperature control occurs, leading to particle growth to the desired size; (iv) stopping the crystallization by solvent removal; and (v) optionally, a step of isolating the processed ingredients in the form of powder.

Figure 6:
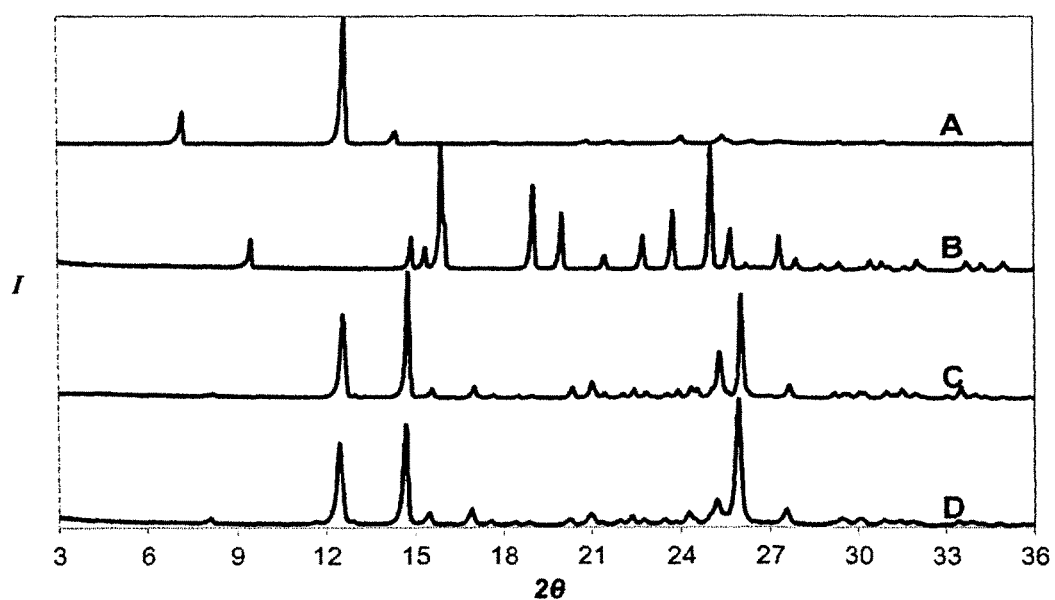

FIG. 6 is a graph of XRPD patterns and normalized intensity (I) of: A) theophylline; B) saccharin; C) theophylline-saccharin co-crystals before drying; and D) theophylline-saccharin after drying.

A product of interest in the present invention can be one or more active pharmaceutical ingredient (API) and the term includes both intermediate and final active ingredients, as well as final APIs which have been processed as part of a formulation or pre-formulation process. The term also includes one or more excipients used to formulate the API as a bulk intermediate drug product. One or more APIs alone, or in combination with one or more excipients can be present in the suspension of the process.

According to the present invention, there is provided a process for controlling the particle size, while controlling the particle size distribution, of one or more active pharmaceutical ingredients (APIs), or one or more APIs with one or more excipients, which process comprises:
 a) suspending particles of the one or more APIs and optionally one or more excipients in a mixture of at least two solvents that comprise at least a first solvent and a second solvent; wherein at least the first solvent partially dissolves at least one of the APIs and/or excipients;
 b) reducing the size of the particles in the suspension produced in step a);
 c) crystallizing the partially dissolved product by aging the suspension at an appropriate temperature and during a specific period of time;
 d) stopping the aging by removing the first solvent Preferably, the process is for reducing the particle size, while controlling the particle size distribution, of one or more active pharmaceutical ingredients (APIs), or one or more APIs with one or more excipients.

Preferably, the second solvent comprises an anti-solvent of the at least one API and/or excipient dissolved or partially dissolved in the first solvent. The term "anti-solvent" as used herein with reference to a particular substance is used to describe a solvent that said substance is substantially insoluble in. When a substance is mixed with its anti-solvent, the substance is suspended within the anti-solvent as opposed to dissolving within in. Preferably, the term is used to refer to a solvent in which said substance is completely insoluble. What is considered an anti-solvent for a particular substance would be known to the skilled person.

Preferably, the first solvent is present in proportions of first solvent/second solvent of from 2:1 to 0.01:1 w/w, and optionally from 1:4 to 0.1:1 w/w. The step d) of removing the first solvent can comprise any suitable step known to the skilled person for removing said solvent. Preferably, step d) of removing the first solvent comprises distillation, drying, filtration, or any combination thereof.

The step of particle size reduction carried out in step b) can be any suitable particle size reduction step. Such methods are known to the skilled person. Preferably, the particle size reduction of step b) is performed by high pressure homogenization, microfluidization, ball milling, high shear mixing, or any combination thereof. The step of crystallization of the dissolved portion by aging in step c) preferably comprises allowing the suspension to stand and age for a period of time. The step of aging in step c) is preferably carried out for a time period sufficiently long enough for particle size growth to occur. Preferably, this particle size growth occurs via Ostwald ripening. Preferably, the step of crystallization through aging with appropriate temperature control in step c) comprises allowing the suspension to stand for at least 1 hour. The particles of one or more APIs or one or more APIs with one or more excipients can be present in any suitable amount. Preferably, the particles of one or more APIs or one or more APIs with one or more excipients are present in the suspension in an amount of 30% w/w or less, preferably 15% w/w or less, and most preferably 10% w/w or less.

In a further aspect of the present invention, the solubilized portion of the product of interest crystallizes on the surface of the undissolved particles, eliminating the formation of an amorphous portion and thereby maintaining the degree of crystallinity of the polymorphic form of interest and resulting in a more stable product.

According to another aspect of the invention, there is provided the use of the active pharmaceutical ingredients, or API with excipients, when made according to the process of the invention for the preparation of therapeutically useful medicaments.

According to another aspect of the invention, there is provided a particle comprising one or more APIs, or a particle comprising one or more APIs and one or more excipients, wherein the particle is obtainable by the process of the present invention.

According to another aspect of the invention, there is provided a particle comprising one or more APIs or a mixture of one or more APIs and one or more excipients characterized by a particle size distribution span of less than 2.5. Preferably, the one or more APIs or a mixture of one or more APIs and one or more excipients have a particle size distribution span of less than 1.8, and more preferably less than 1.5. This invention addresses the overall limitations described above for patent WO2011131947, namely:
 i) In addition to the processing of API(s) enabling the particle engineering of drug substances, it also enables the processing of mixtures of API(s) with excipients known to a person skilled in the art to yield intermediate drug product(s);
 ii) In addition to maintaining the API polymorphic form, this process can also be applied in a controlled manner to generate new polymorphic forms, such as co-crystals;
 iii) This process eliminates the requirement of selecting the perfect anti-solvent (which may not exist) as it comprises the use of a mixture of solvents in which at least one of them partially dissolves the API and/or the excipients; in other words, the present invention uses to advantage the limitation existing in WO2011131947, as the partial solubilization is promoted, so that it might by subsequently beneficially controlled;
 iv) Moreover, the use of solvent mixtures with the characteristics described in (iii) presents the advantage of enabling the fine-tuning of the affinity/polarity between the solvent, the API/excipients and the micronization equipment. For example, when processing tiotropium bromide according to WO2011131947, severe adherence of the product to the walls of the equipment and product agglomeration was observed, making the process unfeasible. This phenomenon was overcome with the process of this invention.
 v) It comprises a step of aging leading to particle growth, which allows overcoming particle size over reduction that conducts to batch failure. This is a major limitation of all micronization processes, such as high pressure homogenization, microfluidization, ball milling, high shear mixing or other wet milling technologies known by a person skilled in the art.
 vi) It allows obtaining narrow particle size distributions and an improved control of the particle size as a consequence of the aging/crystallization step. The most common approach for expressing particle size results is to report Dv10, Dv50, and Dv90 values based on a volume distribution. The span calculation [(Dv90−Dv10)/Dv50] is the most common format to express distribution width. That said, the present invention also provides a new strategy to control independently these parameters, resulting in a higher performance material suitable for instance for inhalation grade materials.

The present invention thus provides products with improved particle size control, and improved particle size distribution control, and in particular, a smaller particle size distribution span.

The terms Dv10, Dv50, and Dv90 as discussed herein are known to those skilled in the art. Dv50 refers to the maximum particle diameter below which 50% of the sample volume exists. Dv90 refers to the maximum particle diameter below which 90% of the sample volume exists. Dv10 refers to the maximum particle diameter below which 10% of the sample volume exists. The term particle size distribution span refers to the result of the calculation [(Dv90−Dv10)/Dv50].

In the process of the present invention the aging step is driven by the partial solubility of the API (or excipients) in the solvent mixture followed by precipitation and controlled crystallization by Ostwald ripening. Ostwald ripening is a known phenomenon in which smaller particles in solution dissolve and recrystallize on the surface of larger particles in order to reach a more thermodynamically stable state, wherein the surface to area ratio is minimized leading to overall crystal growth. Multiple approaches have been developed to avoid this phenomenon in suspensions, and surfactants are commonly used to eliminate or reduce this occurrence. Patent application PT106738 refers to a process to eliminate or reduce this undesired phenomenon without the need for stabilizing agents, in which high pressure homogenization is used at mild energy conditions to stabilize the suspension while isolating by spray drying. The present process unexpectedly takes advantage of the undesired Ostwald ripening phenomenon with a controlled aging step for achieving the target particle size and particle size distribution. To control this phenomenon the suspension is allowed to stand over a minimum induction period of time, during which the growth rate is controlled by the particle size after micronization, by solvent/anti-solvent proportion and by temperature.

Thus, contrary to prior art top down particle size engineering processes which have sought to minimize Ostwald ripening so as have obtain more particle size control, the inventors of the present invention have undertaken a new approach whereby the Ostwald ripening phenomenon is actually used to exhibit control of the particle size and particle size distribution.

U.S. Pat. No. 6,379,459B1 discusses Ostwald ripening, whereby a supersaturated solution (with respect to the crystals) can be used to promote Ostwald ripening with the final goal of obtaining calcite or other minerals with uniform size. The process refers to a supply controlled growth terminated by a reaction poisoning step but no details are given how this effect is achieved. Moreover, the process is applied to inorganic materials while the present invention applies to organic pharmaceutical substances. Another distinct feature of the present invention is that the particle growth is terminated by removing the solvent that partially dissolves one of the ingredients by means of a distillation, drying or filtration.

Liu et. al. (Physical Review Letters, 19 Jan. 2007) describes a bottom-up precipitation approach to prepare β-Carotene nanoparticle formulations. The nanoparticles were generated from supersaturated solutions of β-carotene with a block co-polymer in mixtures of tetrahydrofuran (THF) and water at different ratios, in which THF is the solvent and water is the anti-solvent. The initial particle size and particle size growth is controlled by the anti-solvent/solvent ratio. According to Liu et. al., the block co-polymer is required for nanoparticles stabilization, preventing particle growth by agglomeration. Thus, Ostwald ripening is minimized by means of using a block co-polymer, acting as surfactant.

The present invention differentiates from Liu et. al. on the following points:
i) No co-polymer is required to stabilize the suspension.
ii) The suspension is prepared using a top-down approach while Liu et al. reports a precipitation (bottom up) from supersaturated solutions. In the present invention supersaturation, and consequently Ostwald ripening, is originated by combining the API solubility enhancement, in the solvent mixture, with the ability to promote supersaturation oscillations in the particle size reduction step. Supersaturation oscillations are driven by particle size reduction, temperature oscillations, shear stress of the material, amongst other factors.
iii) Liu et al. refers to the preparation of nanoparticles while the current invention reports the production of microparticles. The skilled person would understand the term nanoparticle as used herein, in a broadest sense, to refer to particles with a largest diameter of from about 1 nanometer to about 1 micrometer. Preferably, however, the skilled person would understand the term nanoparticles to refer to particles with a largest diameter of from about 1 nanometer to about 100 nm. The skilled person would understand the term microparticle, as used herein, in the broadest sense, to refer to a particle with a largest diameter of from about 0.1 to about 100 micrometers. Preferably, the skilled person would understand the term microparticle to refer to particles with a largest diameter of from about 1 micrometer to about 100 micrometers.
iv) The current invention takes advantage of the Ostwald ripening phenomenon to control the particle size while Liu et al. aims to develop nanoparticles formulations and provides a method to evaluate the stability of formulations.

In regards to other bottom-up approaches for particle engineering, controlled crystallization strategies have considered (i) a large amount of seeds to promote uniform crystal growth, (ii) providing rapid micromixing to avoid local high supersaturation and (iii) supply enough energy input to prevent agglomeration. The process of using seeds to control the crystallization of APIs is known and described in patent US2009/0087492 where seeds are produced by micronization in suspension, forming a slurry that is introduced in the crystallization process. Such process is capable of producing particles with mean particle size of less than 100 microns; however in order to ensure a narrow particle size distribution, homogeneity of the seeds is a requirement but in general this approach tends to yield broad distributions.

Other technologies have also been proposed for the preparation of uniformly distributed particles, as described in patent application WO2013144554, namely through coupling suspension particle size reduction with membrane filtration.

Although the technology enables narrow particle size distributions, a membrane filtration step needs to be included, adding complexity to the overall process.

The current art is therefore lacking in solutions where there is a need to reduce the particle size of an API and/or excipients in a liquid medium, while achieving a high degree of particle size control, reproducibility and polymorphic control, without complex and costly engineering.

The current invention can be applied to attain precise control of particle size including, but not restricted to amorphous, crystalline, hydrated or solvated forms of active pharmaceutical ingredients and pharmaceutical acceptable salts thereof prone to polymorphic transformation when using traditional particle size reduction technologies, such as most corticosteroids and other active pharmaceutical ingredients.

It is envisaged that the process of the present invention can be used to process a great variety of different active pharmaceutical ingredients. Preferably, the APIs that are processed in the process of the present invention comprise corticosteroids and antibiotics. Examples of such APIs are: mometasone and esters thereof (e.g., mometasone furoate, mometasone furoate monohydrate), fluticasone and esters thereof (e.g. fluticasone propionate, fluticasone furoate), tiotropium (e.g. tiotropium bromide, tiotropium bromide monohydrate), ciclesonide, budesonide, formoterol, salmeterol, salbutamol, beclomethasone and esters thereof (e.g beclomethasone dipropionate), betamethasone and esters thereof (e.g betamethasone acetate), ipratropium, terbutaline, hydrocortisone and esters thereof (e.g. hydrocortisone 17-propionate 21-acetate), fosfomycin, tobramycin, doxycycline minocycline, ciprofloxacin, vancomycin, rifampicin, gentamicin, amphotericin, azithromycin or combinations of two or more of these active pharmaceutical ingredients.

Finally, it will be noted that the present invention can also be used to produce particles comprising two or more compounds (APIs or excipients), known as intermediate drug products, where at least one will remain partially suspended during the process and act as a substrate and the other will dissolve and will then recrystallize on the surface of the substrate, by means of the described process.

Suitable excipients used in this invention for the purpose of preparing intermediate drug products would be known to the skilled person. It is envisaged that a variety of different excipients can be used in the process of the present invention along with a variety of different APIs to produce a variety of different intermediate drug products. Preferably, the excipients are selected from the group comprising surfactants, amino acids, lipids waxes, fatty acids, sugars, flavoring agents, polymers, or combinations thereof. The excipients may be varied depending on the desired formulations and applications. Examples include, but not exclusively, the microencapsulation or coating of APIs to protect from oxidation or light degradation or to improve dissolution, cohesion/adhesion, flowability, surface energy and/or surface area, etc. The selection of suitable excipients and the quantity to be used is within the expertise of a person skilled in the art using routine trial and experimentation.

It will also be noted that the present invention is applicable to any compound where there is a need to reduce particle size, or alter particle characteristics (such as surface area, surface energy, surface rugosity, morphology, shape, rate of charge decay, adhesion, cohesion and adhesion/cohesion balance) and achieving narrow spans.

Co-crystals are an example of intermediate drug products that can be engineered according to the present invention. Co-crystals are multi-component crystals synthesized through controlled crystallization of at least two molecules (e.g. an API and a co-former) to achieve a stable molecular complex. The resulting co-crystal has different physical properties than the crystalline API. Examples include, but not exclusively, bioavailability, performance, compressibility, stability, hygroscopicity, etc.

Fernández-Ronco et al. (Cryst. Growth Des. 2013, 13, 2013-2024) report the preparation of a model pharmaceutical co-crystal by simultaneous high pressure homogenization of solid API and co-former in the presence of a surfactant. The surfactant is mandatory for co-crystal formation and to avoid particle agglomeration during the high pressure homogenization process. The present invention discloses a process that can be applied to the production of co-crystals by particle engineering of mixtures of API with suitable excipients as given in example 3.

As will be clear to the skilled person, APIs or intermediate drug products made in accordance with the process of the present invention may be incorporated into therapeutically useful pharmaceutical compositions which include appropriate excipients where necessary. For example, powder formulations may be produced by blending particles of an API powder produced by the invention with a suitable particulate excipient such as lactose, or any other appropriate excipient (mannitol, glucose, trehalose, etc) for delivery to the lung or nose. The particles of the invention may be also formulated as a suspension for use in a delivery device such as a pressurized canister with a valve-based dose-metering mechanism or for use as a nebulizer or a dry-powder inhaler for pulmonary delivery. Also, intermediate drug products may be further formulated as solid oral dosage forms.

The present invention provides a process for tailoring both particle size and polymorphic form of an active pharmaceutical ingredient or a drug product intermediate that comprise one or more active pharmaceutical ingredients and one or more excipients. The process preferably comprises five steps:

(i) Suspension of one or more ingredients in a mixture of at least two solvents where at least one solvent (referred to hereafter as the first solvent) partially dissolves one of the ingredients. Preferably, the solvent that does not dissolve the one or more ingredients (referred to hereafter as the second solvent) is an anti-solvent of the ingredient that is at least partially dissolved in the first solvent. Preferably, the first solvent/second solvent proportion is from 2:1 to 0.01:1 w/w, more preferably from 1:4 to 0.1:1 w/w. The concentration of API and/or excipients in suspension is preferably below 30% w/w, more preferably below 15% w/w, and most preferably below 10% w/w. The term partial solubility, in a broadest sense, means that the active ingredient and or excipients dissolve in the solvent in proportions of 5,000 volumes or more of solvent/g of solute. Preferably, this term means that the active ingredient and or excipients dissolve in the solvent in proportions of 10,000 volumes or more of solvent/g of solute, and most preferably, 15,000 volumes or more of solvent/g of solute.

(ii) Particle size control of the suspension prepared in (i), preferably by means of high pressure homogenization, microfluidization, ball milling, high shear mixing or other wet milling technologies known by a person skilled in the art. The suspension is processed using the required number of steps to achieve the target particle size in the size reduction step. Preferably, the particle size control comprises particle size reduction.

(iii) A step of crystallization through aging. Preferably, this step comprises allowing the suspension to stand over a period of time. Preferably, this period of time is sufficient for particle size growth to occur. The particle size growth preferably occurs via the process of Ostwald ripening. Preferably, the suspension is allowed to stand for a period of at least one hour. This period of time promotes crystal growth and additional control of the particle size. The period of time that the suspension is aged is sometimes for 3 to 4 days. The aging is preferably performed at a temperature below 60° C., at atmospheric pressure. The size of the particles and the particle size distribution during both the particle size reduction step and the ageing step is monitored. Suitable techniques to monitor the particle size and distribution are known to the skilled person.

(iv) A step where crystallization through aging is stopped by removing the solvent that partially dissolves one of the ingredients. Preferably, this step comprises distillation, drying or filtration until the residual content of the solvent is preferably below 5% w/w, preferably below 1% w/w.

(v) Optionally, a step of isolating the processed ingredients in the form of powder wherein the isolation step preferably comprises filtration and/or a drying step, preferably spray drying.

It will be known to the skilled person which solvent systems are suitable for a particular API, excipient, or combination thereof. Typical solvent systems are for example mixtures of water and acetone, for processing corticosteroids such as fluticasone propionate, mometasone furoate, ciclesonide, budesonide, betamethasone acetate, beclomethasone dipropionate and hydrocortisone 17-propionate 21-acetate. In these cases the solvent in which the API is partially soluble is acetone. Other solvents include dimethylformamide, dimethylacetamide, ethanol, methanol and other alcohols.

For processing tropanes, like tiotropium bromide, aclidinium bromide, umeclidinium bromide or ipatropium bromide, typical solvents systems include mixtures of alkanes, such as n-heptane, with esters, such as ethyl acetate.

For processing substituted benzene derivative class of compounds like formoterol, salmeterol and salbutamol typical solvent systems are mixtures of water and alcohols such as isopropanol.

For processing quinoline derivatives such as indacaterol, typical solvent systems include mixtures of esters, such as ethyl acetate with alcohols, like methanol.

For processing antibiotics such as tobramycin, typical solvent systems include mixtures of esters, such as ethyl acetate with alcohols, like methanol.

Figure 1:
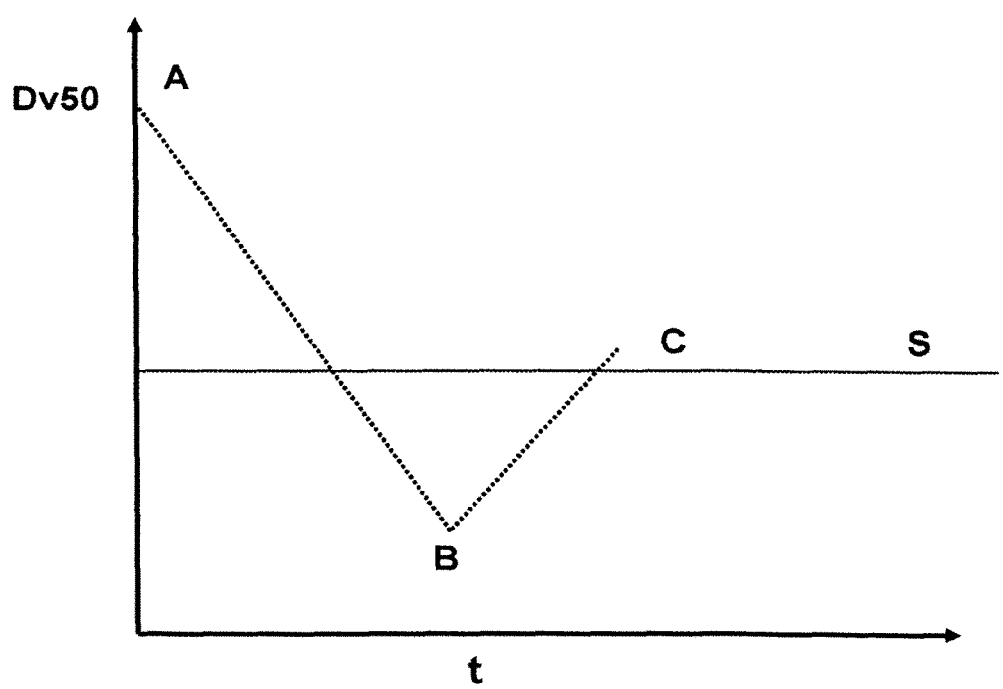
FIG. 1 is a schematic representation of the particle size after: A) suspension preparation step; B) particle size reduction step; and C) crystallization step by aging over the course of time (t) until the target particle size is obtained (S).

In FIG. 1 it is shown a schematic representation of this process. During this process, a suspension of an active pharmaceutical ingredient and/or excipients with an initial particle size (point A) is prepared in a mixture of solvents; then the material is micronized (below the target values—point B) and after an aging period, due to Ostwald ripening, crystals grow (point C) until the target particle size (S). At this point, aging is stopped by means of distillation, drying or filtration technologies known by a person skilled in the art.

Figure 2:
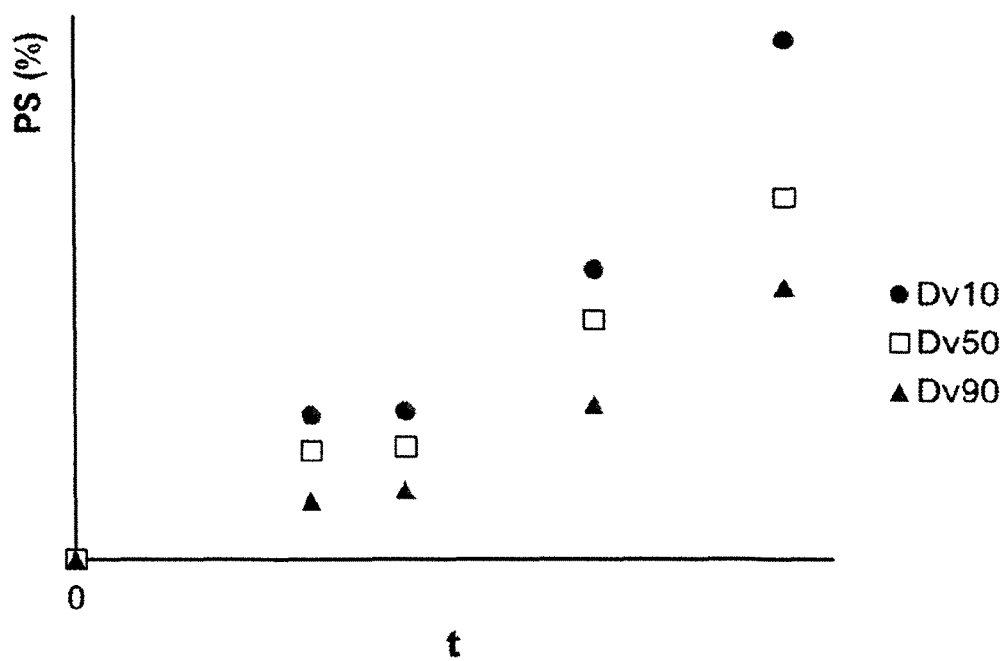
FIG. 2 is a graph of tiotropium bromide normalized particle size (PS) growth during the crystallization by aging step through the course of time (t).
Figure 3:
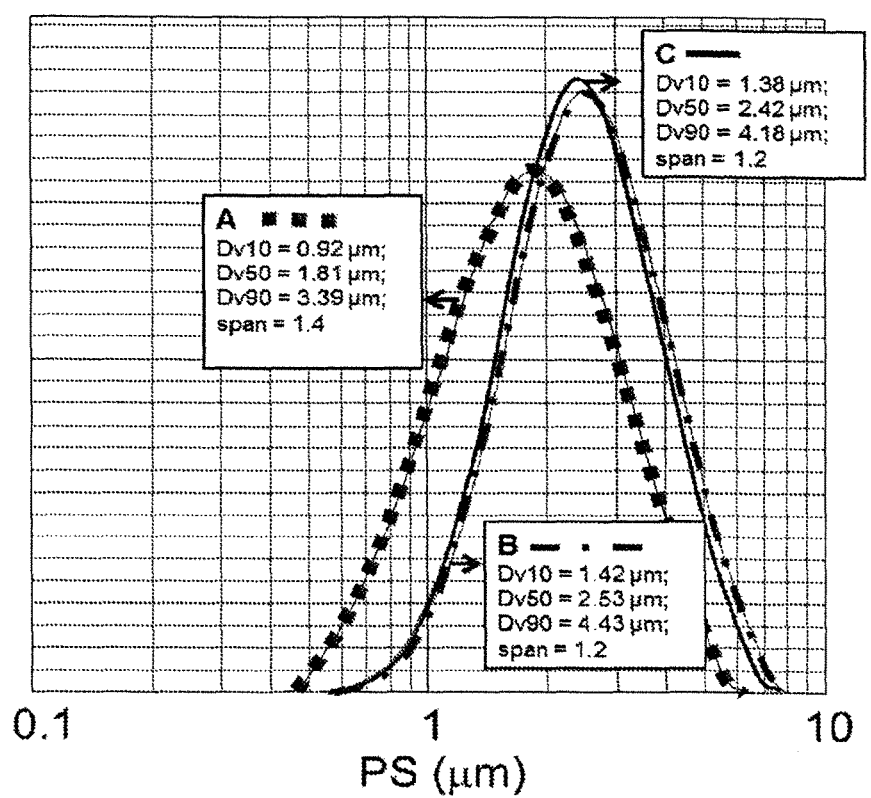
FIG. 3 is a graph of fluticasone propionate particle size (PS) distribution curves obtained according to the invention: A) after particle size reduction; B) after aging step; and C) after isolation via spray drying.
Figure 4:
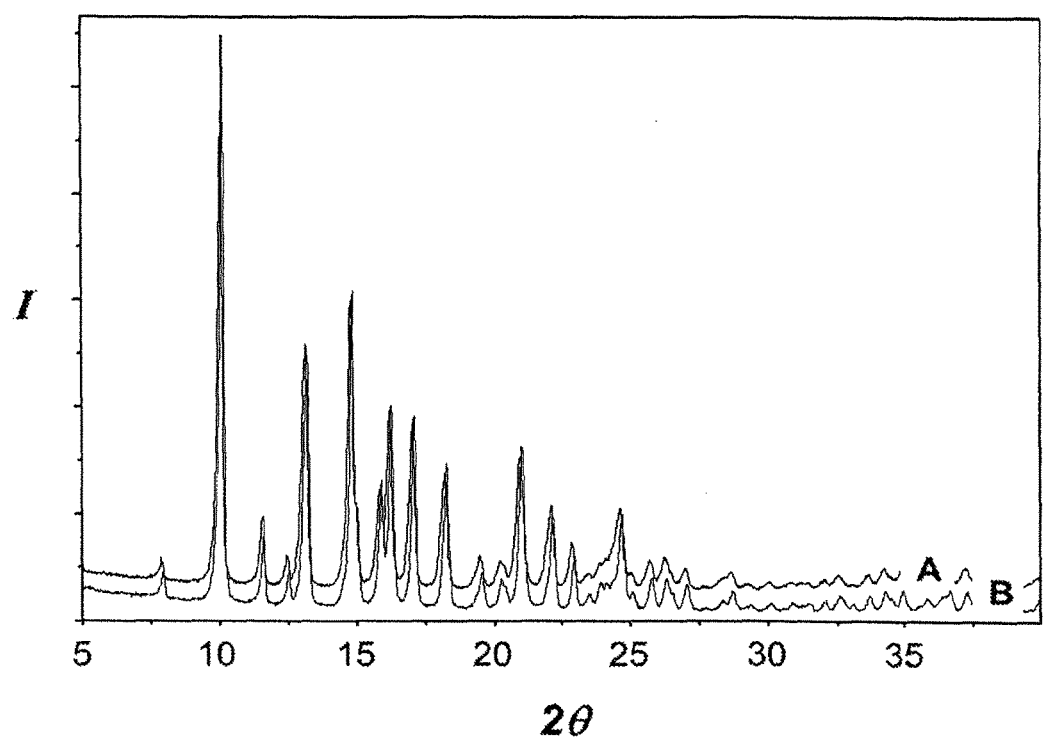
FIG. 4 is a graph of XRPD patterns and normalized intensity (I) of fluticasone propionate after isolation by spray drying step according to the patent application WO2011131947 (A) and according to the invention (B).
Figure 5:
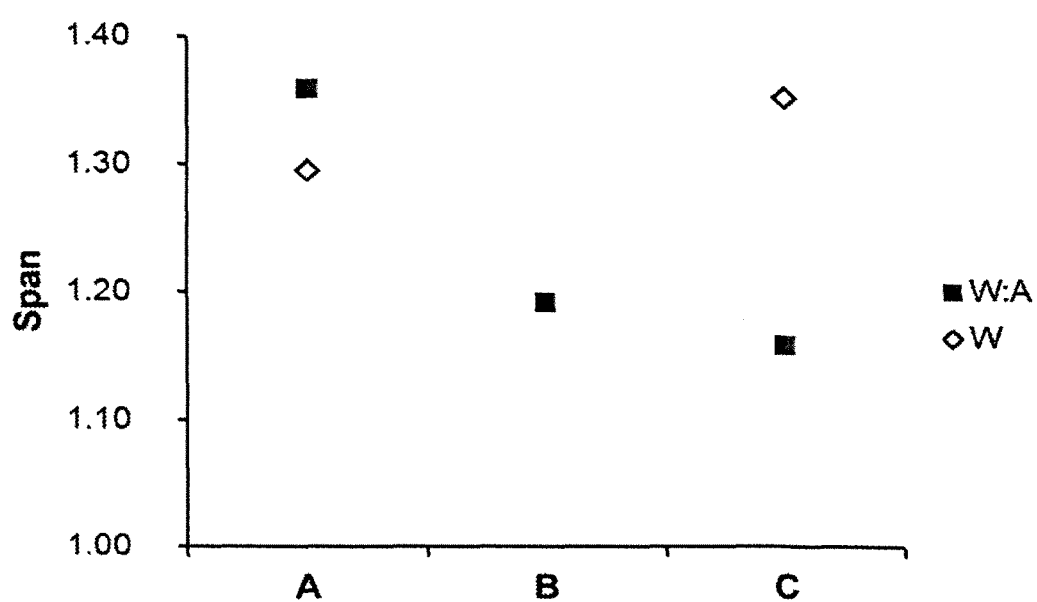
FIG. 5 is a graph of fluticasone propionate particle size distribution span obtained according to the invention, in a water:acetone (W:A) suspension, and in comparison to patent application WO2011131947, in a water (W) suspension, after: A) particle size reduction step; B) crystallization by aging step; and C) isolation via spray drying step.

During the aging step, as represented in FIG. 2, the particle size variation is more pronounced in the Dv10 compared to Dv50 and Dv90, resulting in a narrower particle size distribution (smaller span) and a product of superior performance. In addition, it is also part of the scope of this invention a process to stop the crystal growth as described previously.

EXAMPLE 1

Tiotropium Bromide (40 g) was suspended in a mixture of n-heptane (304 g) and ethyl acetate (456 g) and stirred until a uniform suspension was obtained and fed to a lab scale microfluidizer processor where the suspension was submitted to pressures of 400 bar for 50 cycles. The following particle size results were obtained: Dv10=0.67 µm; Dv50=2.98 µm; Dv90=7.09 µm; span=2.2. After this particle size reduction step, the suspension was transferred to a holding vessel were it was left aging for 20 hours, during which particle size increased, (Dv10=0.78 µm; Dv50=3.33 µm; Dv90=7.45 µm; span=2.0) without stirring at room temperature. After this period, the proportion of ethyl acetate and heptane was changed to approximately 100% heptane by means of a distillation to reduce the amount of material dissolved in suspension. The suspension was fed to a lab scale spray dryer while stirring, with a feed rate of 6 ml/min and a drying temperature of 100° C. The product was collected in a glass flask yielding 30 g.

The product isolated presented an XRPD identical to the one of the starting material and a particle size distribution with Dv10=0.83 µm; Dv50=3.02 µm; Dv90=7.05 µm; span=2.1, which is a size distribution suitable for formulation into an inhalable compound and an appropriate deposition in the lung after inhalation delivery.

EXAMPLE 2

Fluticasone propionate (15 g) was suspended in a mixture of water (256.5 g) and acetone (28.5 g) and stirred until a uniform suspension was obtained and fed to a lab scale microfluidizer processor in which the suspension was submitted to pressures of 750 bar for 45 cycles. The following particle size results were obtained: Dv10=0.92 µm; Dv50=1.81 µm; Dv90=3.39 µm; span=1.4. After this particle size reduction step, the suspension was transferred to a holding vessel where it was left aging for 22 hours, resulting in a larger particle size and a narrower span (Dv10=1.42 µm; Dv50=2.53 µm; Dv90=4.43 µm; span=1.2). After this period, the suspension was fed to a lab scale spray dryer while stirring, with a feed rate of 6 ml/min and a drying temperature of 45° C. The product was collected in a glass flask yielding 12 g.

The product isolated presented an XRPD identical to the one of the starting material and a particle size distribution with Dv10=1.38 µm; Dv50=2.42 µm; Dv90=4.18 µm; span=1.2, which is a size distribution suitable for formulation into an inhalable compound and an appropriate deposition in the lung after inhalation delivery FIG. 3 presents the narrow particle size distribution curves of fluticasone propionate obtained after the three main steps of this invention (particle size reduction, aging and isolation).

For comparison, the process disclosed in patent WO2011131947 was applied to the processing of fluticasone propionate. Fluticasone propionate (30 g) was suspended in the anti-solvent water (270 g) and stirred until a uniform suspension was obtained and fed to a lab scale microfluidizer processor in which the suspension was submitted to pressures of 750 bar for 45 cycles. The following particle size results were obtained: Dv10=1.28 µm; Dv50=2.44 µm; Dv90=4.45 µm; span=1.3. After this size-reduction step, the suspension was fed to a lab scale spray dryer while stirring, with a feed rate of 6 ml/min and a drying temperature of 45° C. The product was collected in a glass flask yielding 19 g.

The product isolated presented an XRPD identical to the one obtained by the present invention (FIG. 4) and a particle size distribution with Dv10=0.99 µm; Dv50=1.94 µm; Dv90=3.60 µm; span=1.4.

As observed in FIG. 5 the final powder particle size distribution curve obtained using the invention herein disclosed was narrower (span ~1.2) than the distribution curve obtained with process described in patent WO2011131947 (span ~1.4).

EXAMPLE 3

As an example of the processing of API and excipients, theophylline (4.03 g) and saccharin (4.09 g) were suspended in a mixture of water (367.8 g) and ethanol (32.2 g). Stirring proceeded until a uniform suspension was obtained. Finally the suspension was processed in a lab scale microfluidizer processor submitted to pressures of 755 bar for 25 cycles. After this particle size reduction step, the suspension was transferred to a holding vessel where it was left aging for 48 hours without stirring at room temperature. After this period, the suspension was fed to a lab scale spray dryer while stirring, with a feed rate of 10 ml/min and a drying temperature of 65° C.

The product isolated presented the target crystalline form of theophylline-saccharin co-crystal as described by Enxian et al. (CrystEngComm, 2008, 10, 665-668). FIG. 6 presents the XRPD of the product (before and after drying) and the corresponding raw materials.

The product particle size had a distribution with Dv10=2.03 μm; Dv50=4.60 μm; Dv90=8.76 μm; span=1.5.

The invention claimed is:

1. A process for controlling the particle size, while controlling the particle size distribution, of one or more active pharmaceutical ingredients (APIs), or one or more APIs with one or more excipients, which process comprises:
   a) suspending particles of the one or more APIs and optionally one or more excipients in a mixture of at least two solvents that comprise at least a first solvent and a second solvent; wherein at least the first solvent partially dissolves at least one of the APIs and/or excipients, wherein the API and/or excipient are soluble in the first solvent in an amount of 5,000 volumes or more of solvent per gram of solute, and wherein the API and/or excipient are substantially insoluble in the second solvent;
   b) reducing the size of the particles in the suspension produced in step a);
   c) aging the suspension by allowing the suspension to stand over a period of time of at least one hour so as to allow particle size growth to occur via Ostwald ripening;
   d) stopping the aging by removing the first solvent.

2. The process according to claim 1, wherein the process is for reducing the particle size, while controlling the particle size distribution, of one or more active pharmaceutical ingredients (APIs), or one or more APIs with one or more excipients.

3. The process according to claim 1, wherein the second solvent comprises an anti-solvent of the at least one API and/or excipient partially dissolved in the first solvent.

4. The process according to claim 1, wherein the first solvent is present in proportions of first solvent/second solvent of from 2:1 to 0.01:1 w/w.

5. The process according to claim 1, wherein the first solvent is present in proportions of first solvent/second solvent of from 1:4 to 0.1:1 w/w.

6. The process according to claim 1, wherein step d) of claim 1 of removing the first solvent is performed by distillation, drying, or filtration, or any combination thereof.

7. The process according to claim 1, wherein the particle size reduction of step b) of claim 1 is performed by high pressure homogenization, microfluidization, ball milling, or high shear mixing, or any combination thereof.

8. The process according to claim 1, wherein the suspension is processed using the required number of steps to achieve the target particle size.

9. The process according to claim 1, wherein step d) of claim 1 comprises distillation performed until the first solvent is removed.

10. The process according to claim 1, wherein step d) of claim 1 comprises a membrane filtration until the first solvent is removed.

11. The process according to claim 1, further comprising the step of isolating the products of the process in the form of powder wherein the isolation step comprises a filtration and/or a drying step.

12. The process according to claim 1, further comprising the step of isolating the products of the process in the form of powder wherein the isolation step comprises spray drying.

13. The process according to claim 1, wherein the products of the process have a particle size distribution with a span selected from the group consisting of less than 2.5, below 1.8 and below 1.5.

14. The process according to claim 1, wherein the process is a top down production process.

15. The process according to claim 1, wherein the particles produced by the process comprise microparticles.

16. The process according to claim 1, wherein the one or more APIs comprise one or more corticosteroids.

17. The process according to claim 1, wherein the one or more APIs comprise one or more antibiotics.

18. The process according to claim 1, wherein the one or more APIs is selected from a group consisting of mometasone, fluticasone, tiotropium, ciclesonide, budesonide, formoterol, salmeterol, salbutamol, beclomethasone, betamethasone, ipratropium, terbutaline, hydrocortisone, fosfomycin, tobramycin, doxycycline minocycline, ciprofloxacin, vancomycin, rifampicin, gentamicin, amphotericin, and azithromicin or combinations thereof.

19. The process according to claim 1, wherein the one or more excipients is selected from a group consisting of surfactants, amino acids, lipids, waxes, fatty acids, sugars, flavoring agents, and polymers, or combinations thereof.

20. The process according to claim 1, wherein the concentration of APIs and excipients in the suspension is selected from the group consisting of 30% w/w or less, 15% w/w or less, and 10% w/w or less.

21. The process according to claim 1, wherein the API and/or excipient are soluble in the first solvent in an amount of 10,000 volumes of solvent per gram of solute.

22. The process according to claim 1, wherein the one or more APIs comprise tiotropium bromide, the first solvent is an ester formed from the reaction of a $C_1$ to $C_5$ alcohol and a $C_1$ to $C_5$ carboxylic acid, and the second solvent is a $C_1$ to $C_9$ alkane.

23. The process according to claim 1, wherein the one or more APIs comprise tiotropium bromide, the first solvent is ethyl acetate and the second solvent is heptane.

24. The process according to claim 1, wherein the one or more APIs comprise fluticasone propionate, the second solvent is water, and the first solvent is a $C_1$ to $C_6$ ketone.

25. The process according to claim 1, wherein the one or more APIs comprise fluticasone propionate, the second solvent is water and the first solvent is acetone.

* * * * *